United States Patent [19]

Moore et al.

[11] 4,114,620
[45] Sep. 19, 1978

[54] PATIENT TREATMENT PAD FOR HOT OR COLD USE

[75] Inventors: Francis Claudell Moore; Leon Raymond Perkinson, both of Indianapolis, Ind.

[73] Assignee: Moore-Perk Corporation, Indianapolis, Ind.

[21] Appl. No.: 773,673

[22] Filed: Mar. 2, 1977

[51] Int. Cl.² .............................................. A61F 7/00
[52] U.S. Cl. ..................................... 128/254; 128/400
[58] Field of Search ............... 128/254, 399, 400, 402, 128/296, 403

[56] References Cited

U.S. PATENT DOCUMENTS

| 2,110,022 | 3/1938 | Kliesrath | 128/400 X |
| 2,726,658 | 12/1955 | Chessey | 128/400 |
| 3,463,161 | 8/1969 | Andrassy | 128/402 |
| 3,867,939 | 2/1975 | Moore et al. | 128/254 |

Primary Examiner—John D. Yasko
Attorney, Agent, or Firm—Larry N. Barger

[57] ABSTRACT

A medical pad with a pair of laminated plastic film panels defining a passage therebetween for circulating hot or cold water. The pad has a patient contact panel of long staple absorbent cellulosic fibers, and these fibers are anchored directly to a plastic film panel or are intertwined and locked to similar fibers that are so anchored. For moist therapy, the patient contact pad is wetted immediately before use.

13 Claims, 7 Drawing Figures

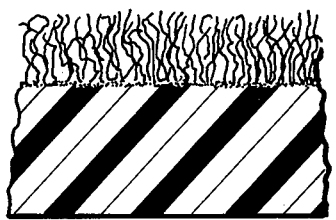
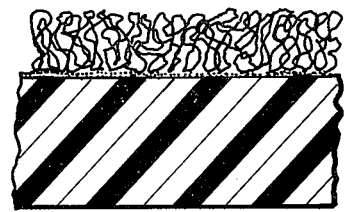
FIG. 4      FIG. 5
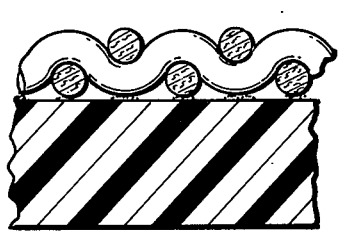
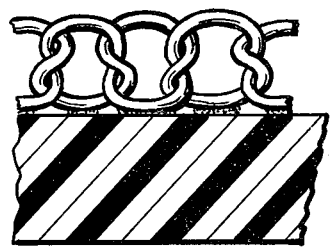
FIG. 6      FIG. 7

PATIENT TREATMENT PAD FOR HOT OR COLD USE

BACKGROUND OF THE INVENTION

In our previous U.S. Pat. No. 3,867,939, we disclosed a disposable laminated pad for applying hot or cold therapy to a patient. This pad had two thermoplastic film panels secured together to define between them a circulating passage for hot or cold water. To an outer surface of this pad was secured a highly absorbent material, such as a soft paper of the quality used in facial tissue. Because the fibers of such absorbent material were not adequately anchored to the laminated plastic film conduit, it was necessary to incorporate a nonabsorptive grid, such as spun bonded nylon to an outer surface of the absorptive paper material or the like. This grid material was secured to the absorptive paper panel by laminating and partially melting a thin polyethylene film between the nonabsorptive grid and the absorptive paper. The purpose of the nonabsorptive grid material was to provide structural strength to the patient contacting surface of the medical pad. These pads often bear the full weight of the patient as he shifts his weight and moves about on the pad. When one recognizes that the absorptive material was similar to two layers of facial tissue, it is easy to recognize the requirement for the strong nonabsorptive grid material to protect the absorptive material, particularly when wetted for moist therapy.

Others have proposed various constructions for applying a soft comfortable patient contact surface on thermal pads. A typical approach is to use a slip cover over the pad, similar to putting a pillowcase over a hot water bottle. Some slip covers are sewn shut to permanently encase the heating pad. In heating pads which include water circulating tubes, opposite sides of the slip cover are sometimes stitched together with thread in an area between the circulating tubes.

U.S. Pat. No. 2,110,022 describes a covering for a thermal pad that is of cotton, linen, silk or the like. From the drawings and descriptions in this patent, this covering is believed to be of the pillow case slip cover construction described above. There is no mention of any surface to surface bonding of the cloth cover to the encased portions of the thermal pad. FIG. 3 of this patent shows a slight gap between the cloth covering and the encased portions of the pad. This patent fails to describe any securement of the cloth covering. If there were any securement, it would logically be by stitching with thread between the refrigerant circulating tubing. This is because large areas of the cloth covering lie against either a wool blanket 24 or loose cotton filling 32. A surface to surface bond between the cloth covering and these materials would be extremely difficult, making stitching by thread a logical choice, if indeed any securement of the cloth covering were desired.

Others have also proposed the pillow case or slip cover construction to thermal pads. In U.S. Pat. No. 2,250,325 a covering is secured by stitching 18. Also, in U.S. Pat. No. 3,211,216 a slip cover is shown stitched together at 13 between the encased refrigerant circulating tubing.

Another type of covering for a thermal pad was proposed in U.S. Pat. No. 2,726,658. In FIG. 3, a waterproof envelope of rubberized fabric is shown encasing the cooling liquid circulating tubing. This covering material would be inoperative for moist therapy because being "waterproof" it would repel rather than absorb water. This rubberized fabric envelope would have a construction similar to galoshes or rubberized workers' goves that begin with a cloth lining that is then rubber coated.

SUMMARY OF THE INVENTION

In the present invention, we have provided a patient treatment pad with an improved patient contact panel that is highly flexible, has a soft feel, is lint resistant, is highly liquid absorptive for moist therapy, and exhibits a very high wet strength. The patient treatment pad includes two laminated thermoplastic film panels sealed together at selected locations to define a water circulating passage therebetween, and also provides a strong thermoplastic bonding surface for support of an absorptive patient contact panel. The patient contact panel comprised of long staple liquid absorptive fibers is bonded to one thermoplastic film panel at closely spaced locations in a surface to surface bond. These absorptive fibers are several times longer than the thickness of the patient contact panel and are intertwined among themselves in a manner which tends to lock the fibers together through various twist turns, kinks, etc. throughout their long length. With this construction, the absorptive fibers are physically anchored to the thermoplastic supporting panel at a surface to surface bond, or are intertwined and locked to other similar fibers that are anchored to the thermoplastic film. Thus, the structural support of a nonabsorptive grid material required for the physical stength and structural integrity of the absorptive facial tissue layer in our previous U.S. Pat. No. 3,867,939 is not needed in the construction of the present invention.

BRIEF DESCRIPTION OF THE DRAWINGS

FIG. 4 is a further enlarged sectional view similar to FIG. 3 showing fibers bonded to a film panel;

FIG. 5 is a view similar to FIG. 4, but showing filaments;

FIG. 6 is a view similar to FIG. 4, but showing a woven fabric; and

FIG. 7 is a view similar to FIG. 4, but showing a knitted fabric.

DETAILED DESCRIPTION

Figure 1:
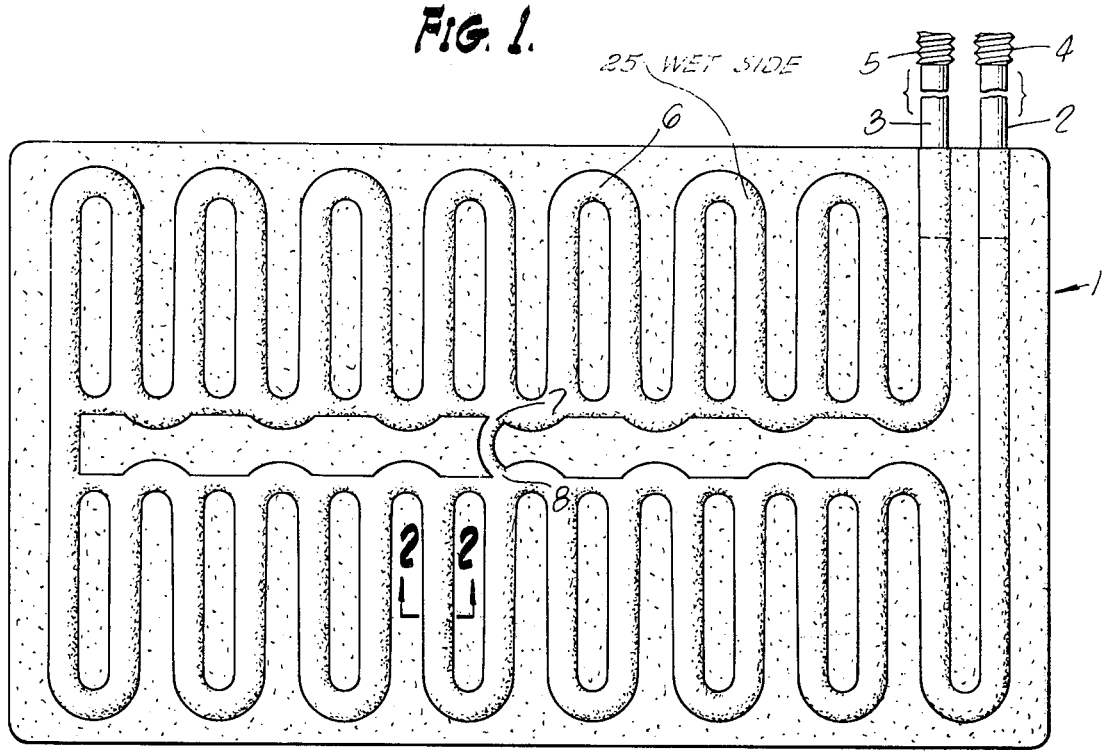
FIG. 1 is a top plan view of the patient treatment pad.

In FIG. 1 the patient treatment pad 1 is shown connected to lead tubes 2 and 3 which respectively have connectors 4 and 5 for joining to a water temperature control and circulating unit (not shown). Hot or cold liquid is circulated through tubes 2 and 3 which are in communication with each other through a serpentine conduit 6 in the body of the treatment pad itself. If desired, bridging passages 7 and 8 can be provided between adjoining passages in the conduit pattern. Should a section of the patient treatment pad be folded to crimp off flow through a particular section of the serpentine pattern, circulating liquid can shunt across a bridge at 7 or 8 and thereby maintain flow through a portion of the pad.

Figure 2:
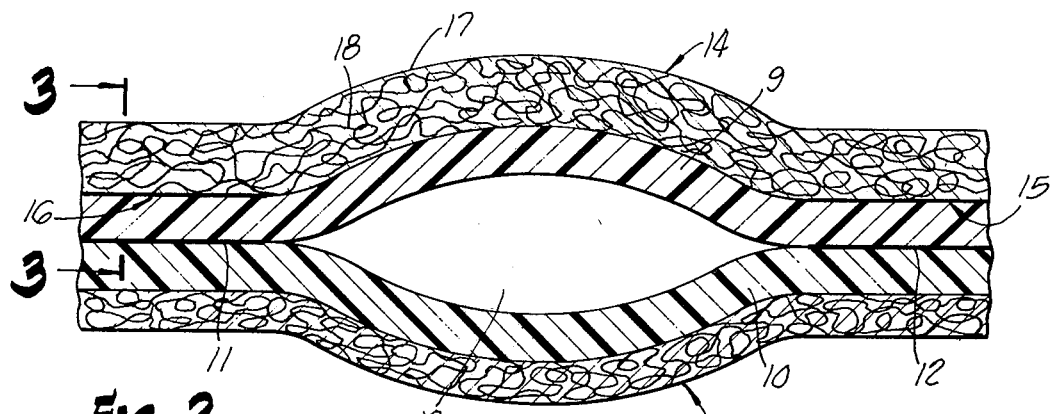
FIG. 2 is an enlarged sectional view taken along lines 2—2 of FIG. 1.
Figure 3:
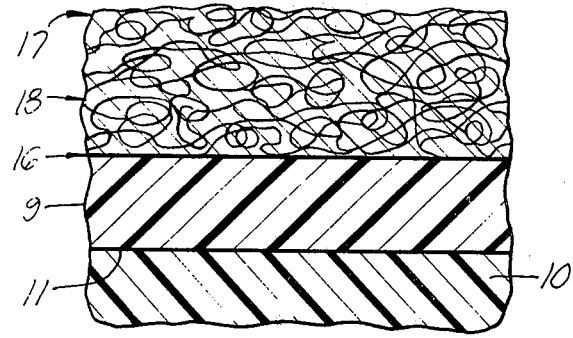
FIG. 3 is an enlarged sectional view taken along lines 3—3 of FIG. 2.

FIG. 2 shows the construction of the pad which includes a pair of thermoplastic panels 9 and 10 sealed together at 11 and 12 by conductive heat fusion from a hot die, or by R.F. sealing, to provide a liquid passage area 13. These thermoplastic panels 9 and 10 can be of polyurethane, polyvinyl chloride, or other suitable polymer. Overlying thermoplastic panel 9 is an absorptive patient contact panel 14 which is preferably used for moist therapy, but can also be used for applying dry therapy. Absorptive panel 14 is secured to thermoplastic panel 9 in a surface to surface bond area formed by conductive heat fusion, R.F. sealing, or a waterproof adhesive, such as 15 and 16 located throughout the pad.

This absorptive panel 14 is comprised of long staple absorptive fibers which have an average length several times greater than the thickness of absorptive panel 14. These fibers in the physical form of a woven panel, nonwoven panel, or knitted panel are exposed on a patient contact surface 17. Because of the long length of the fibers, they are anchored to the thermoplastic panel 9 at the various surface to surface bonds, such as shown at 15 and 16 in FIG. 2. The long fibers extend into a central area such as 18 of panel 14. Here the fibers either extend through panel 14 and are directly anchored to the thermoplastic panel at the surface to surface bonds, such as 16, or intertwine with similar fibers anchored to the thermoplastic film 9. Thus, because the long absorptive fibers are anchored to thermoplastic film 9, the highly absorptive layer 14 can withstand substantial frictional abuse through patient movement, etc. while moist and still not disintegrate. This fiber anchoring feature also reduces linting in the absorptive layer. There is no need for a nonabsorptive grid on the patient treatment surface to prevent disintegration and delamination of the absorptive layer.

On an opposite side of the patient treatment pad is a second absorptive panel 20. Panel 20 is similar to panel 14, but preferably is of a thinner and lighter weight for quick thermal conductivity for dry therapy. Such dry therapy panel could have a weight of 10 to 50 gms./sq. yd. Preferably, panel 20 is of one color, such as blue, and labeled for dry therapy, with the term "DRY SIDE". Panel 14 can be of a different color, such as white, and labeled for wet therapy, as shown at 25 with the term "WET SIDE". This panel could have a weight of 25 to 50 gms./sq. yd. By simply reversing sides of the pad, it is convenient to switch back and forth between wet and dry therapy as the need arises.

We have found that the absorptive panel 14 works very well when constructed of a nonwoven fabric of 80% rayon and 20% cotton (Novenette 9812 marketed by Kendall Corporation) and has a weight of 82 gms./sq. yd. Patient contact panel 20 is preferably of a nonwoven fabric of 100% polyester material marketed by Kendall Corporation under the name Novenette #6106, and has a weight of 28 gms./sq. yd.

While both sides of the treatment pad can be used for either dry therapy or moist therapy, it is preferred to use the thicker heavier side for moist therapy because this side of the pad will hold more water. The thinner lighter side is preferably used for dry therapy because without the liquid heat conducting medium the thinner material acts as less of an insulator.

In the foregoing specification, reference has been made to liquid absorptive fibers of a patient contact panel. It is not fully understood precisely how these fibers absorb liquid. Liquid could be absorbed directly into the cellular structure of each individual fiber causing it to swell, or the liquid could be held by a surface attraction to the fibers. It is not important precisely how this absorption takes place. Throughout the specification and claims, absorption is intended to refer to the fibers collectively rather than individually. Absorption is intended to mean the capacity to hold a substantial amount of water making the pad's surface wet to the touch. A spun bonded nylon would be considered nonabsorptive for the purpose of a patient treatment pad even though nylon may absorb a small amount of water. Nylon would not blot up liquid and be wet to the touch.

Throughout the specification the terms "fiber" and "staple" have been used to define construction of the patient contact surface. It is understood that a fabric of extruded filaments would fall within the scope of this invention, provided such filaments were highly liquid absorptive and anchored at a surface to surface bond to the thermoplastic film of the conduit. These fibers or filaments could be of a natural or synthetic material or mixtures thereof.

The exposed elongated liquid absorptive means bonded to the panel can have various forms, such as fibers in a nonwoven material (FIG. 4); extruded filaments in a nonwoven material (FIG. 5); woven fabric (FIG. 6); or a knitted fabric (FIG. 7). It is understood that both the woven and knitted forms can be made of threads, yarns, or the like that include fibers or filaments which bond to the film panel.

In the foregoing specification, specific examples have been referred to to explain the invention. It is understood by those skilled in the art that certain modifications can be made to these examples without departing from the spirit and scope of the invention.

We claim:

1. A patient treating pad for wet or dry use comprising: a pair of superimposed film panels with inner surfaces joined together at selected locations to define a fluid circulating path between the film panels; a patient contact panel secured at a surface to surface bond to one of the film panels; and said patient contact panel has an outer patient contact surface of exposed elongated liquid absorptive means selected from the group consisting of fibers and filaments that extend into a central portion of the patient contact panel and are anchored to the film panel at the surface to surface bond.

2. A patient treating pad as set forth in claim 1, wherein the liquid absorptive means are fibers that have an average length of more than twice the thickness of the patient contact panel.

3. A patient treating pad as set forth in claim 1, wherein the patient contact panel has a thickness in the range of 0.005 to 0.050 inch and the liquid absorptive means are fibers with a length in the range of 0.1 to 1.5 inch.

4. A patient treating pad as set forth in claim 1, wherein the liquid absorptive means has a physical form selected from the group consisting of nonwoven panel, woven panel, and knitted panel.

5. A patient treating pad as set forth in claim 1, wherein the patient contact panel is of a cellulosic material selected from the group consisting of rayon, cotton, and mixtures thereof.

6. A patient treating panel as set forth in claim 1, wherein the film panel is a thermoplastic, and the surface to surface bond with the patient contact panel is a heat fusion joint.

7. A patient treating pad as set forth in claim 1, wherein the surface to surface bond is a water-resistant adhesive joint.

8. A patient treating pad as set forth in claim 1, wherein both film panels of a thermoplastic material with a patient contact panel in a surface to surface bond to each film panel; indicia means on one panel to show it is for wet treatment; and indicia means on the other panel showing it is for dry treatment.

9. A patient treating pad as set forth in claim 8, wherein the wet patient contact panel is of a material having a weight of 25 to 150 gms./sq. yd. and the dry patient contact panel is of a material having a weight of 10 to 50 gms./sq. yd.

10. A patient treating pad as set forth in claim 1, wherein the patient contact panel is of a material selected from the group consisting of natural material, synthetic material, and mixtures thereof.

11. A patient treating pad as set forth in claim 1, wherein the elongated liquid absorptive means are entwined fibers, some of which are anchored to the panel at the surface to surface bond and such bonded fibers in turn secure other fibers to the panel through this intertwining relationship.

12. A patient treating pad as set forth in claim 1, wherein the elongated liquid absorptive means are filaments that extend completely through the patient contact panel and are anchored at the surface to surface bond.

13. A patient treating pad for wet or dry use comprising: a pair of superimposed thermoplastic film panels with inner surfaces joined together at selected locations to define a fluid circulating path between the film panels; a nonwoven patient contact panel secured at a heat fusion joint to one thermoplastic panel; and said patient contact panel has an outer patient contact surface of exposed long staple liquid absorptive fibers that extend into a central portion of the patient contact panel and are anchored to such panel in a heat fusion joint; and such heat fusion joint being superimposed over a heat fusion joint between the inner surfaces of the two thermoplastic panels.

* * * * *